US00PP28277P3

(12) United States Plant Patent
Misato

(10) Patent No.: US PP28,277 P3
(45) Date of Patent: Aug. 15, 2017

(54) ***MANDEVILLA* PLANT NAMED 'SUNPAPRI'**

(50) Latin Name: *Mandevilla hybrida*
Varietal Denomination: Sunpapri

(71) Applicant: SUNTORY FLOWERS LIMITED, Tokyo (JP)

(72) Inventor: Tomoya Misato, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 25 days.

(21) Appl. No.: 14/998,488

(22) Filed: Jan. 9, 2016

(65) Prior Publication Data

US 2017/0202123 P1 Jul. 13, 2017

(51) Int. Cl.
*A01H 5/02* (2006.01)

(52) U.S. Cl.
USPC ..... Plt./232

(58) Field of Classification Search
USPC ..... Plt./232
See application file for complete search history.

*Primary Examiner* — Keith Robinson
(74) *Attorney, Agent, or Firm* — C. A. Whealy

(57) ABSTRACT

A new and distinct cultivar of *Mandevilla* plant named 'Sunpapri', characterized by its vining plant habit; vigorous growth habit; freely branching habit; dark green-colored leaves; early and freely flowering habit; long flowering period; and medium-sized light to pale orange-colored flowers.

1 Drawing Sheet

Botanical designation: *Mandevilla hybrida.*
Cultivar denomination: 'SUNPAPRI'.

BACKGROUND OF THE INVENTION

The present invention relates to a new and distinct cultivar of *Mandevilla* plant, botanically known as *Mandevilla hybrida* and hereinafter referred to by the name 'Sunpapri'.

The new *Mandevilla* plant is a product of a planned breeding program conducted by the Inventor in Higashiomi, Shiga, Japan. The objective of the breeding program is to create new vining and freely branching *Mandevilla* plants with freely flowering habit and medium- sized attractive flowers.

The new *Mandevilla* plant originated from a cross-pollination in Higashiomi, Shiga, Japan in May, 2009 of a proprietary selection of *Mandevilla hybrida* identified as code number MR-7, not patented, as the female, or seed parent with a proprietary selection of *Mandevilla hybrida* identified as code number 04M11-2, not patented, as the male, or pollen, parent. The new *Mandevilla* plant was discovered and selected by the Inventor as a single flowering plant from within the progeny of the stated cross-pollination in a controlled greenhouse environment in Higashiomi, Shiga, Japan in September, 2010.

Asexual reproduction of the new *Mandevilla* plant by cuttings in Higashiomi, Shiga, Japan since March, 2011 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunpapri'. These characteristics in combination distinguish 'Sunpapri' as a new and distinct *Mandevilla* plant:

1. Vining plant habit.
2. Vigorous growth habit.
3. Freely branching habit.
4. Dark green-colored leaves.
5. Early and freely flowering habit.
6. Long flowering period.
7. Medium-sized light to pale orange-colored flowers.

Plants of the new *Mandevilla* can be compared to plants of the female parent selection. Plants of the new Mandevilla differ primarily from plants of the female parent selection in the following characteristics:

1. Plants of the new *Mandevilla* have larger flowers than plants of the female parent selection.
2. Plants of the new *Mandevilla* and the female parent selection differ in flower color as plants of the female parent selection have red-colored flowers.

Plants of the new *Mandevilla* can be compared to plants of the male parent selection. Plants of the new *Mandevilla* differ primarily from plants of the male parent selection in flower color as plants of the male parent selection have white-colored flowers.

Plants of the new *Mandevilla* can be compared to plants of the *Mandevilla amabilis*×*Mandevilla boliviensis* 'Sunmandeho', disclosed in U.S. Plant Pat. No. 11,556. In side-by-side comparisons conducted in Higashiomi, Shiga, Japan, plants of the new *Mandevilla* differed from plants of 'Sunmandeho' in the following characteristics:

1. Plants of the new *Mandevilla* flowered earlier and for a longer period of time than plants of 'Sunmandeho'.
2. Plants of the new *Mandevilla* were more freely flowering than plants of 'Sunmandeho'.

3. Flower petals of plants of the new *Mandevilla* were roughly ovate in shape whereas flower petals of plants of 'Sunmandeho' were orbicular in shape.
4. Plants of the new *Mandevilla* and 'Sunmandeho' differed in flower color as plants of 'Sunmandeho' had yellowish white-colored flowers with white-colored throats.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph at the top of the sheet comprises a side perspective view of a typical flowering plant of 'Sunpapri' grown in a container.

The photograph at the bottom of the sheet is a close-up view of a typical flowering plant of 'Sunpapri'.

DETAILED BOTANICAL DESCRIPTION

The aforementioned photographs and following observations, measurements and values describe plants grown during the summer in 15-cm containers in an outdoor nursery in Higashiomi, Shiga, Japan and under cultural practices typical of commercial Mandevilla production. During the production of the plants, day temperatures averaged 25° C. and night temperatures averaged 15° C. Plants were six months old when the photographs and detailed description were taken. In the following description, color references are made to The Royal Horticultural Society Colour Chart, 2007 Edition, except where general terms of ordinary dictionary significance are used.

Botanical classification: *Mandevilla hybrida* 'Sunpapri'.

Parentage:

*Female, or seed, parent*.—Proprietary selection of *Mandevilla hybrida* identified as code number MR-7, not patented.

*Male, or pollen, parent*.—Proprietary selection of *Mandevilla hybrida* identified as code number 04M11-2, not patented.

Propagation:

*Type*.—By vegetative cuttings.

*Time to initiate roots*.—About two weeks at temperatures about 23° C. to 25° C.

*Time to produce a rooted young plant*.—About five to six weeks at temperatures about 23° C. to 25° C.

*Root description*.—Fibrous; typically light brown in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Vining plant habit; vigorous growth habit; freely branching habit.

*Plant height*.—About 115 cm.

*Lateral branch description*.—Length: About 85 cm. Diameter: About 2.7 mm. Internode length: About 4.8 cm. Strength: Strong, flexible. Texture: Pubescent, rough. Color, developing: Close to N144C; slightly tinged with close to N170B. Color, fully developed: Close to 177D.

Leaf description:

*Arrangement*.—Opposite, simple.

*Length*.—About 10.5 cm.

*Width*.—About 4.2 cm.

*Shape*.—Oblong.

*Apex*.—Cuspidate.

*Base*.—Obtuse.

*Margin*.—Entire.

*Texture, upper and lower surfaces*.—Smooth, glabrous.

*Luster, upper surface*.—Glossy.

*Luster, lower surface*.—Somewhat glossy.

*Venation pattern*.—Pinnate, reticulate.

*Color*.—Developing leaves, upper surface: Close to between 144A and 146A. Developing leaves, lower surface: Close to 146D. Fully expanded leaves, upper surface: Close to 137B; venation, close to 145A. Fully expanded leaves, lower surface: Close to 146B; venation, close to 145B.

*Petioles*.—Length: About 1.7 cm. Diameter: About 2.5 mm. Texture, upper and lower surfaces: Smooth, glabrous. Color, upper and lower surfaces: Close to 145A.

Flower description:

*Flower type and habit*.—Single salverform flowers arranged in axillary racemes; flowers face mostly outwardly; freely flowering habit with about eleven flowers per inflorescence and about ten inflorescences per plant.

*Natural flowering season*.—Early flowering habit, plants begin flowering about six weeks after planting; long flowering period, plants flower continuously from mid-May until late November in Japan.

*Flower longevity on the plant*.—About seven to ten days; flowers not persistent.

*Fragrance*.—Faintly fragrant, pleasant.

*Inflorescence height*.—About 14.3 cm.

*Inflorescence diameter*.—About 16.8 cm.

*Flowers*.—Appearance: Salverform; flared trumpet, corolla fused and five-parted; flowers roughly star-shaped. Diameter: About 9.4 cm. Depth (length): About 6.7 cm. Tube length: About 4.1 cm. Tube diameter, distally: About 1.4 cm. Tube diameter, mid-section: About 5 mm. Tube diameter, proximally: About 2.7 mm.

*Flower buds*.—Height: About 6.7 cm. Diameter: About 9.8 mm. Shape: Lenticular. Color: Distally, close to 38D; mid-section, close to 13D; proximally, close to 145B.

*Corolla*.—Quantity and arrangement: Five petals arranged in a single whorl and fused towards the base into an elongated tube; petal lobes imbricate. Petal lobe length: About 4.3 cm. Petal lobe width: About 3.7 cm. Petal lobe shape: Roughly ovate, asymmetrical. Petal lobe apex: Acute. Petal lobe margin: Entire; slightly undulate and recurved. Petal lobe texture, upper surface: Smooth, glabrous; velvety. Petal lobe texture and luster, lower surface: Smooth, glabrous; matte. Throat texture: Smooth, glabrous. Tube texture: Smooth, glabrous. Color: Petal lobe, when opening, upper surface: Close to 27A; towards the apex, close to 39C; towards the base, close to 19A. Petal lobe, when opening, lower surface: Towards the apex, close to 23D; towards the base, close to 158A. Petal lobe, fully opened, upper surface: Close to 27C; towards the apex, close to 49B; towards the base, close to 16B. Petal lobe, fully opened, lower surface: Close to 155D. Throat: Distally, close to N25B to N25C with venation, close to 19C; proximally, close to 14B to 14C to 14D with venation, close to 12B. Tube: Distally, close to 4D; mid-section, close to 4C; proximally, close to 150B.

*Calyx*.—Quantity and arrangement: Five sepals arranged in a single whorl, fused at the base; calyx, star-shaped. Sepal length: About 6.4 mm. Sepal width: About 3.8 mm. Sepal shape: Lanceolate. Sepal apex: Acute. Sepal margin: Entire. Sepal texture, upper and lower surfaces: Smooth, glabrous. Sepal color, upper and lower surfaces: Distally, close to 37A; proximally, close to 144D.

*Peduncles*.—Length: About 6.9 cm. Diameter: About 2.5 mm. Texture: Smooth, glabrous. Aspect: Upright to outwardly. Color: Close to 145B.

*Pedicels*.—Length: About 2 cm. Diameter: About 2 mm. Texture: Smooth, glabrous. Aspect: Upright to outwardly. Color: Close to 145A.

*Reproductive organs*.—Stamens: Quantity and arrangement: Typically five; filaments fused to corolla; anthers, connivent. Anther shape: Ellipsoidal. Anther size: About 1 mm by 7 mm. Anther color: Close to 11C. Pollen amount: Moderate. Pollen color: Close to 4D. Pistils: Quantity: Typically one. Pistil length: About 1.2 cm. Style color: Close to 145D. Stigma shape: Rounded. Stigma color: Close to 145C. Ovary color: Close to 145C.

*Seeds and fruits*.—Seed and fruit production have not been observed on plants of the new *Mandevilla*.

Disease & pest resistance: Plants of the new *Mandevilla* have not been noted to be resistant to pathogens and pests common to *Mandevilla* plants.

Garden performance: Plants of the new *Mandevilla* have been observed to tolerate wind, rain and temperatures ranging from about 4° C. to about 30° C.

It is claimed:

1. A new and distinct *Mandevilla* plant named 'Sunpapri' as illustrated and described.

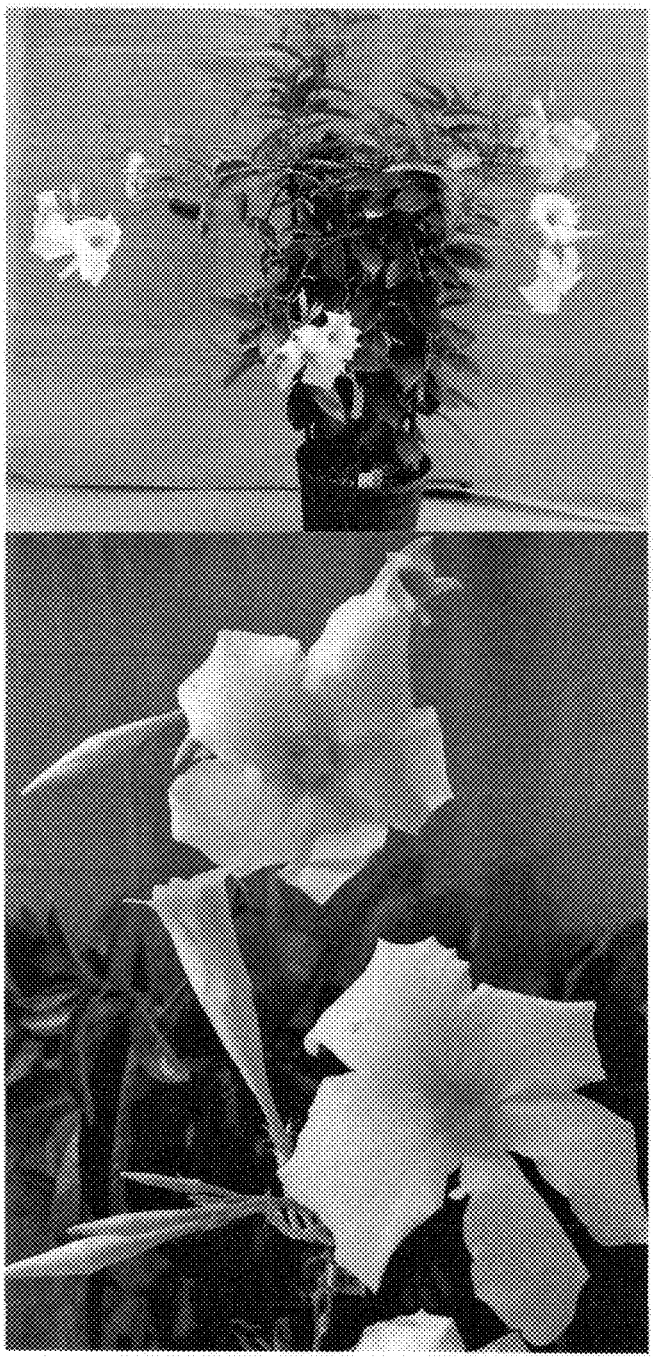

* * * * *